(12) United States Patent
Stack et al.

(10) Patent No.: US 6,322,490 B1
(45) Date of Patent: Nov. 27, 2001

(54) RADIOACTIVE STENT STRUCTURES

(75) Inventors: Richard S. Stack; Kenneth J. Weeks, both of Chapel Hill, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/514,143

(22) Filed: Feb. 28, 2000

Related U.S. Application Data

(63) Continuation of application No. PCT/US98/17331, filed on Aug. 26, 1998.
(60) Provisional application No. 60/056,394, filed on Aug. 26, 1997.

(51) Int. Cl.[7] ........................................ A61N 5/00
(52) U.S. Cl. ................................................. 600/3
(58) Field of Search .................................. 600/1–8

(56) References Cited

U.S. PATENT DOCUMENTS

| | | |
|---|---|---|
| 5,059,166 | 10/1991 | Fischell et al. . |
| 5,199,939 | 4/1993 | Dake et al. . |
| 5,395,300 | 3/1995 | Liprie . |

OTHER PUBLICATIONS

Weeks, "Method for determining photonuclear production of radioisotopes using high–energy electron beams"; Jan. 1999; pp. 49–54.

Weeks et al, "Production of radioisotopes by direct electron activation"; Apr. 1998; pp. 488–492.

Weeks et al; "The Compton backscattering process and radiotherapy"; Mar. 1997; pp. 417–423.

*Primary Examiner*—John P. Lacyk
(74) *Attorney, Agent, or Firm*—Nixon & Vanderhye PC

(57) ABSTRACT

Methods and apparatuses for irradiating stent structures that are selectively collapsible or reducible along their longitudinal axis to reduce the total length thereof are described. Providing a collapsible stent structure reduces the effective surface area which must be exposed to the radiation beam, thereby reducing the time required for the irradiation process. Stent structures suitable for irradiation using the method and apparatus are also described.

22 Claims, 7 Drawing Sheets

RADIOACTIVE STENT STRUCTURES

This application is a continuation of International Application No. PCT/US98/17331, filed Aug. 26, 1998, the disclosure of which is incorporated herein by this reference. This application also claims the benefit of U.S. Provisional Application Ser. No. 60/056,394, which was filed Aug. 26, 1997, the disclosure of which is incorporated herein by this reference.

BACKGROUND OF THE INVENTION

1. Field of the Invention

The present invention relates generally to the production of radioactive stent structures and, more particularly to positioning devices that allow stents to be selectively axially collapsible or reducible to facilitate either mass production or "point-of-use" production of radionuclides by irradiation with intense radiation beams so as to form radioactive stents suitable for therapeutic and/or diagnostic medical purposes.

2. Description of the Related Art

Radioactive materials have been used extensively for many years for therapeutic and/or diagnostic medical purposes. In this regard, radioisotopes are used to kill large volumes of cancer cells directly using large quantities of radioactive material. Alternatively, small amounts of radioisotopes are injected into the body or bloodstream and their position in the body is determined by observing the gamma rays emitted when they decay. Radioisotopes may also be bound to some chemical which is selected for its ability to localize at a problem area in the body thereby aiding in the diagnosis of disease.

Relatively newer therapies propose the use of small amounts of radioactivity to treat small tissue volumes, namely intravascular walls. For example, U.S. Pat. No. 5,059,166 to Fischell et al., the entire content of which is incorporated hereinto by reference, discloses embedding a radioactive isotope material into an existing stent structure, the radioactive material having a half-life of less than 100 days, which stent structure may be embedded into plaque tissue within a patient's arterial wall. The radioactive stent releases radiation so as to decrease the rate of proliferative cell growth of the traumatized arterial wall, i.e., to decrease intimal hyperplasia. As a result of such radiation therapy, restenosis after stent implantation is expected to be significantly reduced.

Another example is the use of esophageal stents to alleviate dysphagia in patients with esophageal cancer. Suppression of tumor regrowth through the stent mesh is a major quality of life concern for these patients. If an easy way of making such stents radioactive can be found, radioactive stents would be utilized.

A further example is the potential use of radioactive stents for the treatment of benign prostatic hyperplasia. Here stents are used to maintain urethral opening. If the stent could simultaneously provide radiation to reduce the affliction causing the stricture this would be advantageous.

Thus, there are many examples where out of control proliferative response (either benign or oncologic) compromises the ability of passageways in the human body to be maintained open. Stents themselves (meaning a rigid mesh structure to provide bracing for the walls) solve the physical-mechanical problem. Radiation from the stent can solve the cellular response that could otherwise grow through the stent and compromise the lumen.

While radiating tissue for medical diagnostic and/or therapeutic purposes is advantageous, there are several real and nontrivial problems associated with such "nuclear medicine", primarily in the availability and/or accessibility of the physician to a source of suitable radioactive devices and materials.

SUMMARY OF THE INVENTION

With the current invention, a cost-effective, reliable technique is being proposed which would enable virtually any facility in need of radioactive stents (for whatever passageway in the body) the ability to produce the same "onsite." Alternatively, it facilitates mass production at a central facility.

In preferred embodiments thereof, the target material is translated relative to the radiation beam along at least two (2) axes. In one example, a target cartridge is provided which includes a tubular shell formed of a material which is minimally, if at all, activated by the radiation beam or, if activated, has radioactivity that is very short lived in terms of minutes or less, e.g., aluminum, tungsten, tantalum. The tubular shell defines an interior hollow space which houses the target material to be irradiated, e.g., an intraluminal stent. The interior space may optionally be filled with a heat transfer fluid, e.g., water, air, an oxygen-less gas or an inert gas. End caps close each end of the tubular shell and are preferably one-piece solid structures formed of the same material as that of the tubular shell. The end caps therefore most preferably serve the purposes of allowing the target cartridge to be mechanically coupled to a translator assembly and provide a path of heat transfer to a heat-transfer fluid, e.g., liquid and/or gas, in contact therewith.

The translator assembly most preferably holds the target cartridge longitudinally so that it is positioned substantially transversely relative to the path of the radiation beam. By suitable adjustment shafts and linear rail assemblies, therefore, the entire target cartridge may be linearly translated simultaneously or periodically, sequentially parallel and perpendicular to the radiation beam path. At the same time, the target cartridge may be rotated about its axis. In such a manner, the target cartridge exposes the target material therewithin uniformly to the radiation beam.

In any irradiating system, depending upon the dimensions of the target material, it may take as long as several hours for the entirety of the target material to be uniformly exposed to the radiation beam. Where the target material is a stent intended for intravascular placement, the time required to irradiate the stent may become a critical factor in respect to the effective use of radioactive stents. Indeed, it is envisioned that a patient would be fully prepared for stent placement in advance of the irradiating procedure. It would be desirable, for the fully prepared patient to wait as little as possible for the stent irradiation process. Therefore, efficient production of radioactive stents would preferentially involve a design and packaging strategy which facilitates the radiation process.

Thus, it is an object of the invention to reduce the time required to irradiate the stent for the purpose of mass production or for "point of care" irradiation at the local clinical facility.

In this regard, Fischell, as noted above, relates to embedding the radioactive isotope material into an existing stent structure, the radioactive material having a half-life of less than 100 days. The present invention, in contrast, relates to the transmutation of inert stent material itself into a radioactive stent and the design of stent structure to optimize the transmutation process. Generation of a stent with short and long half-lives (greater than 100 days) are desirable and their optimum production are disclosed hereinbelow.

The foregoing object is achieved in accordance with the present invention by providing methods for irradiating stent structures that are selectively collapsible or reducible along their longitudinal axis to reduce the total length thereof. Providing a collapsible stent structure reduces the effective surface area which must be exposed to the radiation beam, thereby reducing the time required for the irradiation process. In addition, positioning devices to accomplish the above process are described.

In accordance with one embodiment of the invention, the collapsible stent structure is biased to a longitudinally extended form and is held in its collapsed state during the irradiation process. This enables the radioactive stent to automatically return to its extended disposition, ready for delivery to the patient, thereby minimizing post irradiation manipulation of the stent by medical practitioners and avoiding unnecessary exposure to the radioactive stent.

In the alternative, plunger structures that are selectively detachably coupled to opposite longitudinal ends of the stent may be provided so as to effect the collapse of the stent on urging the plungers towards one another and, likewise, to effect the re-elongation of the stent upon movement of the respective plungers apart. A clamping mechanism or like mechanical attachment to each longitudinal end of the stent together with mechanically controlled collapse and expansion within predetermined parameters may be provided with such an alternative apparatus.

The above described positioning devices will allow a novel method for producing radioactivity in any stent device that is produced from nitinol or any similar shape memory or superelastic material. Such devices all share the property of elasticity that allows temporary longitudinal deformation during irradiation as described below.

These and other objects and advantages of the present invention will become clearer after careful consideration is given to the following detailed description of the preferred exemplary embodiments thereof.

BRIEF DESCRIPTION OF THE DRAWINGS

Reference will hereinafter be made to the accompanying drawings wherein like reference numerals throughout the various FIGURES denote like structural elements, and wherein.

DETAILED DESCRIPTION OF THE PREFERRED EXEMPLARY EMBODIMENTS

Figure 1:
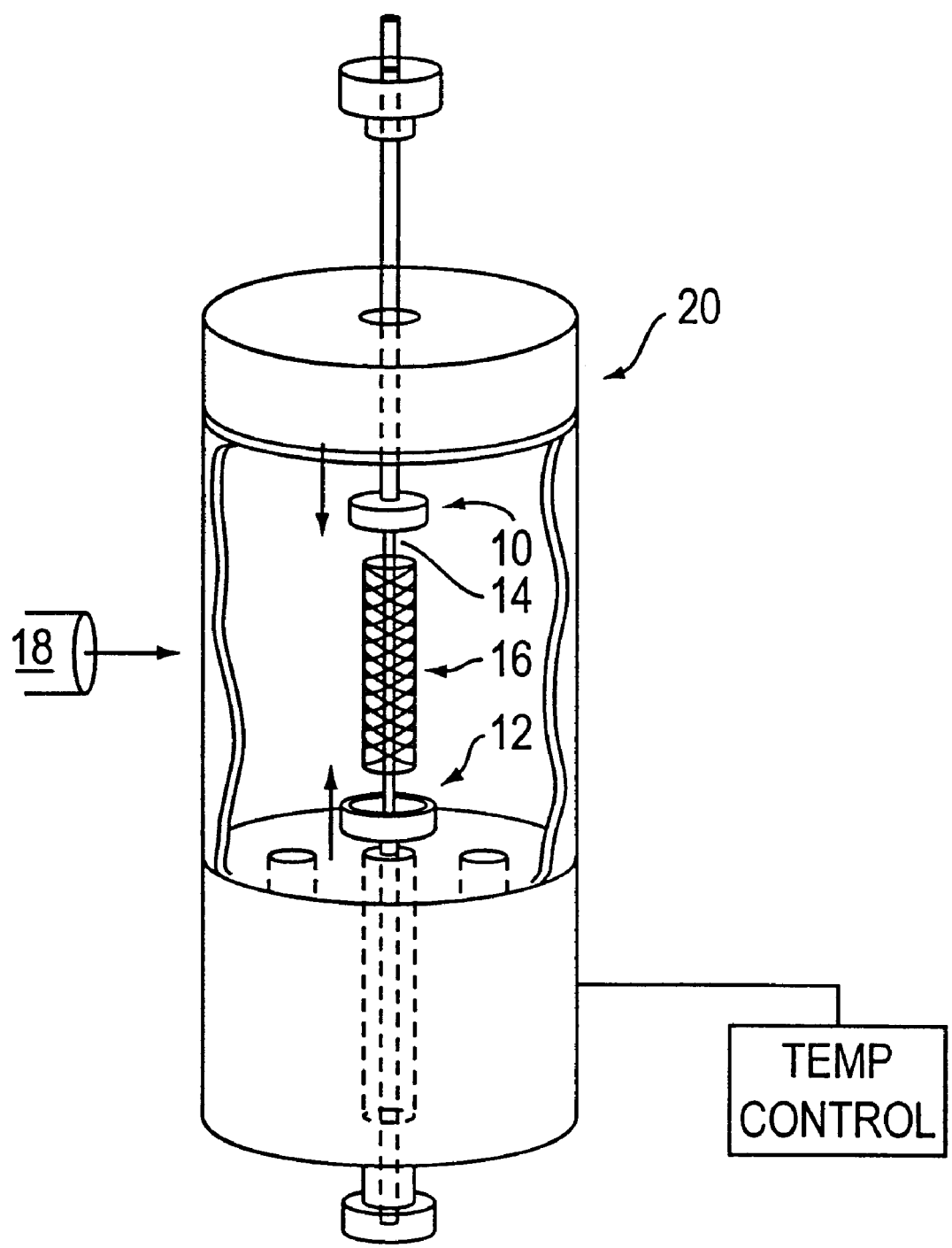
FIG. 1 is a schematic view of a cartridge holder for holding a collapsible stent to be irradiated by a radiation beam.

A presently preferred system for the irradiation process is described by Weeks in Provisional Application No. 60/030, 282, filed Nov. 5, 1996 and entitled PRODUCTION OF RADIONUCLIDES BY INTENSE ELECTRON BEAMS, which corresponds to U.S. application Ser. No. 08/963,068, filed Nov. 3, 1997, and was published as WO09822073, the entire disclosure of which is incorporated herein by this reference.

The following non-limiting Example will further illustrate the present invention.

EXAMPLE

In a preferred embodiment, the stent material is a nickel-titanium alloy (nitinol). The nickel component is 50%. The 58Ni component of the natural nickel is 68%. Absorption of photons by the 58Ni can result in emission of a neutron resulting in 57Ni production, whose half life is 1.5 days. The radiation beam is an intense electron beam with energy 25 MeV.

Absorption of photons in titanium can also result in emission of a proton from 48Ti resulting in 475c, whose half life is 3.3 days. Absorption of photons in 58Ni can also result in emission of a proton resulting in 57Co, whose half life is 272 days. Absorption of photons can also result in emission of deuterons and alpha particles with far lesser probability. For simplicity, the production of 57Ni is considered in detail to illustrate the art of generating radiation dose producing isotopes for therapeutic purposes. The dose from the other isotopes is calculated by the same method. In a particular embodiment, electron linear accelerator have been designed to produce 2 kW, 25 MeV electron beams. These electrons are used to generate electromagnetic energy which in turn causes the emission of nuclear particles from stable target nuclei. This art is well known. The electromagnetic energy ensues from the nature of the electron nucleus interactions known to those skilled in the art as photonuclear and bremsstrahlung.

Although stents of all deployed sizes are envisioned, here, in an illustrative example we consider a stent that will deploy to a diameter of 3.0 mm and a length of 20 mm. This 33 mg nitinol stent is compressed for the irradiation into a space of 0.095 cm inner diameter and 0.1143 cm outer diameter and a length of 4 mm. The 25 MeV electron beam is typically Gaussian shaped with full width half maximum of some 1 mm and nominal diameter of 3 mm. The nitinol stent is enclosed with a high atomic number material (here tantalum, but without loss of efficacy, gold, lead, tungsten, rhenium, alloys of the same, etc). The thickness of tantalum (perpendicular to the electron beam) is 2.5 mm.

Here the high atomic number material is also used to carry away heat by providing a thermal path away from the enclosed stent. This art has been described by Weeks in Provisional Application No. 60/030,282. One finds that 59 microCuries of 57Ni is produced in 10.5 minutes. This is sufficient to produce an average total dose of 10 Gy at a distance of 1 mm from the deployed stent. The dose arises from both positron, electron, and photon emissions from the nickel and other materials (tissues, titanium).

The dose delivered to the wall of the artery varies due to the varying structure of the nitinol metal at the 3.0 mm diameter nominal surface. A complete description of the dose at all distances and relative positions to the internal construction of the stent is possible by repeated application of the Monte Carlo techniques but is not important for the purpose of patent discussed here. Repeating this procedure for all isotopes produced during the bombardment results in a reduced irradiation time. For example, the 48Ti to 47Sc contributes 10% to the average dose at 1-mm distance, thereby reducing the irradiation time by 10%.

It is noted that the inventive nature of the art disclosed here reduces the production time by a factor close to 5. Namely 10 minutes for the compressed stent would be one hour for the same stent, not compressed by the art disclosed here. Thus present art makes production more convenient and hence more practical. Obviously compressing the stent more makes the process even more efficient by bringing more of the stent material into the beam at any one instance. It also reduces the linear extent of the scanning of the stent in the beam (Weeks, Provisional Application No. 60/030, 282).

It will be apparent that the present description may be altered by adjusting any of the parameters described above, thereby making the production slower or faster. These are merely engineering adjustments which would be appreciated by those skilled in the art. For example, boosting the power of the electron beam from 2 kW to a higher value will decrease production time (all else kept the same). The tradeoff is increased cooling load. Increasing the electron energy to 30 MeV electrons will likewise decrease production time. Likewise decreasing these quantities will increase production time. Acceptance of a lower dose to the patient, likewise reduces production time. Increasing the mass of the stent by making it thicker, adding more connectivity etc. decreases production time. All these modifications alter the production times by much less than the compressing of the stent art as disclosed here. Making the target cartridge (tantalum) thicker can reduce the activation rate but can also reduce the cooling load. Thus, a practical embodiment may utilize a 3–5 mm thick tantalum wall to prevent the nitinol stent from rising in temperature too much.

The use of materials such as rhenium, tantalum (and any of the other materials which were detailed in Weeks) for the stent likewise decreases production time. The preferred embodiment focuses on nitinol because of its biocompatibility and its shape memory characteristics which make it more amenable to the art disclosed here than rhenium and tantalum.

Since the variation and tradeoffs are endless, the method of determining the proportions is described here. It incorporates all variations in parameters important to the art disclosed here. First, calculate the dose at various distances from the deployed shape of stent, according to all the isotopic emissions from the irradiated stent. Monte Carlo programs (such as MCNP-4A, Los Alamos National Laboratory) are appropriate for this determination. Choose a target dose at a given position and divide the former by the latter to ascertain the number of decays (of all the isotopic constituents of the stents produced by the radiation bombardment) required to produce such a dose. Compress the stent into its allowed compressed shape. Encapsulate the stent with its bremsstrahlung converter (a given thickness of tantalum) and use the Monte Carlo method to evaluate the flux (number of particles per unit area per unit energy) crossing the stent per electron emitted from the linear accelerator. Vary the thickness of the bremsstrahlung converter to maximize this flux and minimize the energy absorbed by the stent. Integrate this flux times the experimental cross section (probability of creating a radioisotope) for all isotopic parents considered in the first step of this procedure. This times the emission rate of electrons from the linear accelerator will give the amount of time required to bombard the stentconverter-encapsulation material with electrons to produce a radioactive stent which will deliver a given target dose. Evaluate the time required as commercially feasible and adjust proportions to create the various scenarios for production.

There are a number of well known alternate means of producing radiation beams which may be used to produce radioactive stents. These include electron generators (Weeks, Radionuclide . . . ) and free electron lasers (Weeks Med. Phys. 24, 417–423, 1997), the entire disclosure of which is incorporated herein by this reference. Moreover cyclotrons or particle accelerators can produce high energy protons, neutrons or heavy particles, collision of the same with a compressed stent would increase the yield of radioactivity per given time per given cyclotron output flux. The above radiation beam producing devices are expensive pieces of equipment. A practical method of producing the huge volume of stents required must consider production time for each individual stent as a critical factor. Thus, these methods all benefit from the art described herein.

For a radioactive stent to be advantageous, a sufficient portion of the stent must be irradiated, in a short period of time, and the stent must have adequate flexibility and hoop strength for transluminal placement in a target vessel. Thus, critical to the effective use of radioactive stents, as noted above, is to reduce the time required to irradiate the stent so that the related medical procedure can proceed in parallel to the irradiation without undue delay, which may increase risk for the patient or reduce the efficacy of the stent.

In accordance with the present invention, structures which enable the longitudinal compression of the stent, thereby to reduce the time required to activate the stent are proposed. Stents made from shape memory metal, that can be longitudinally compressed and/or deformed and then, on removal of the compression force, return substantially to their original configuration, as well as stent structures configured to telescopingly collapse from one or both ends, and/or stents that are longitudinally collapsible stents, e.g., of an accordion configuration, are proposed. If necessary or desirable, the stent segments are provided that are spring loaded relative to one another to facilitate return to their fully extended length upon removal of an external force.

In the currently preferred embodiments, the stent structure is either porous or has pores defined therethrough to facilitate side branch and/or vessel sidewall perfusion and encapsulation as appropriate. By way of example, the stent is formed as a mesh.

To collapse the stent, in accordance with one embodiment of the invention, plungers are mounted in telescoping surrounding relation to a central mandrel of the irradiation assembly. The plungers are selectively displaceable relative to the end caps, towards one another, thereby to collapse a stent disposed therebetween and minimize its dimension in the longitudinal direction. More particularly, FIG. 1 illustrates a structure suitable for collapsing a resilient stent having a mesh configuration and for selectively holding the same during the irradiation process, as described in greater detail below. In the illustrated embodiment, plungers 10, 12 are mounted in telescoping, sliding relation with respect to the centering/support mandrel 14. Before the irradiation process begins, the plungers 10, 12 are advanced towards one another so as to collapse the stent 16 therebetween, thereby presenting a stent of reduced dimensions for irradiation with the radiation beam 18. The plungers hold the stent in its collapsed state as the target material container 20 is translated longitudinally and/or rotated relative to the radiation beam, as described by Weeks. The plungers may be themselves be spring biased with respect to the target material holder or may be mechanically, hydraulically, or otherwise advanced to their stent collapsing position.

Upon release of the collapsing force of the plungers, the stent extends to its full length disposition, ready for placement in the patient.

Figure 2:
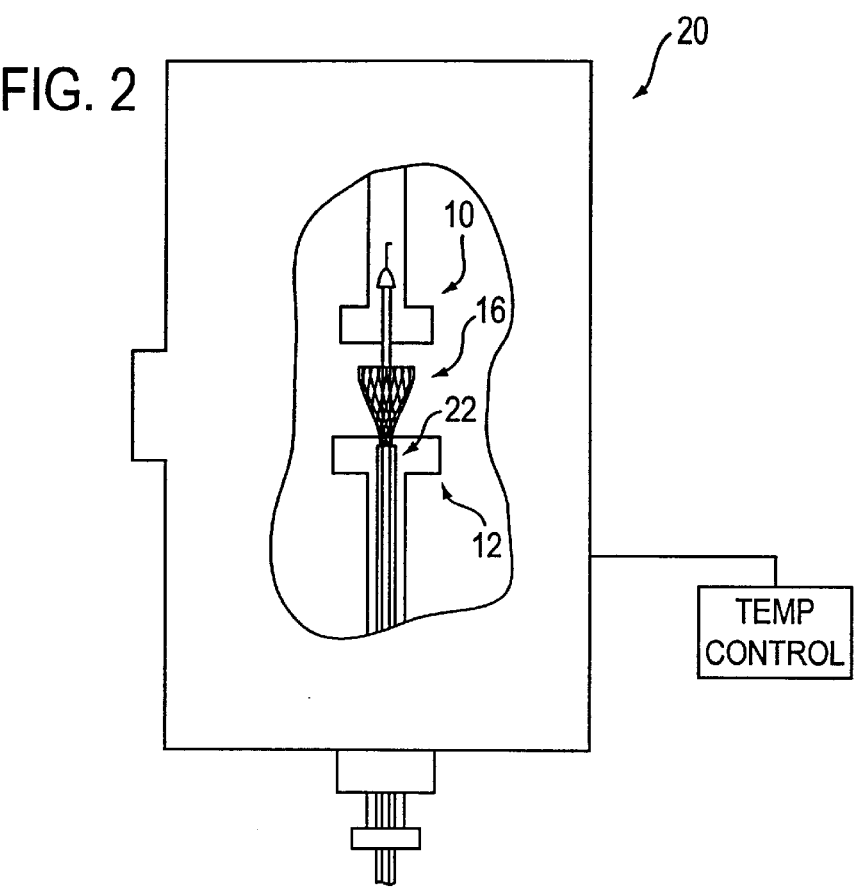
FIGS. 2 and 2A are schematic views showing a stent being deployed in the cartridge holder in advance of irradiation.
Figure 3:
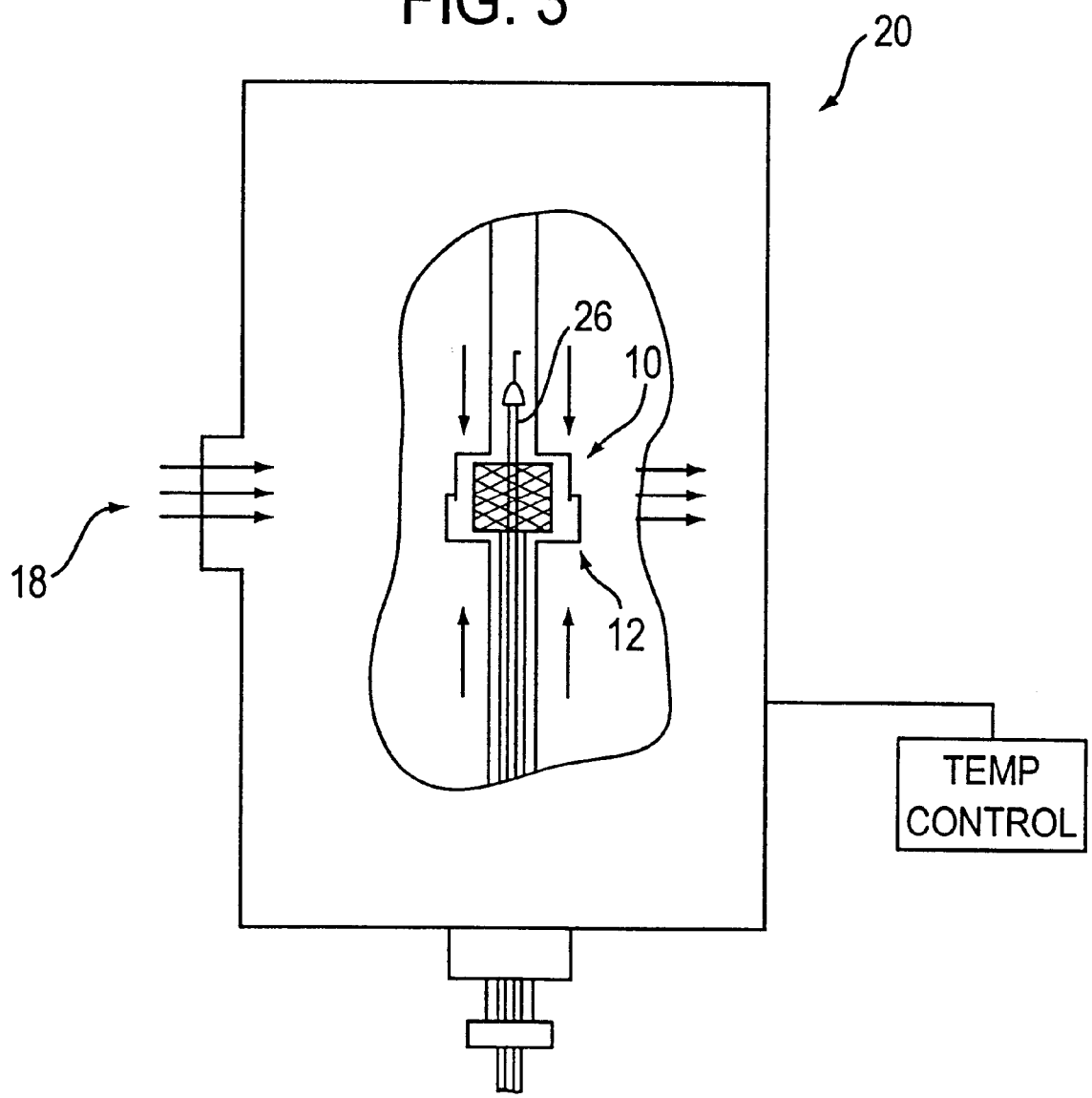
FIG. 3 is a schematic view showing the stent collapsed in the cartridge holder during irradiation.
Figure 4:
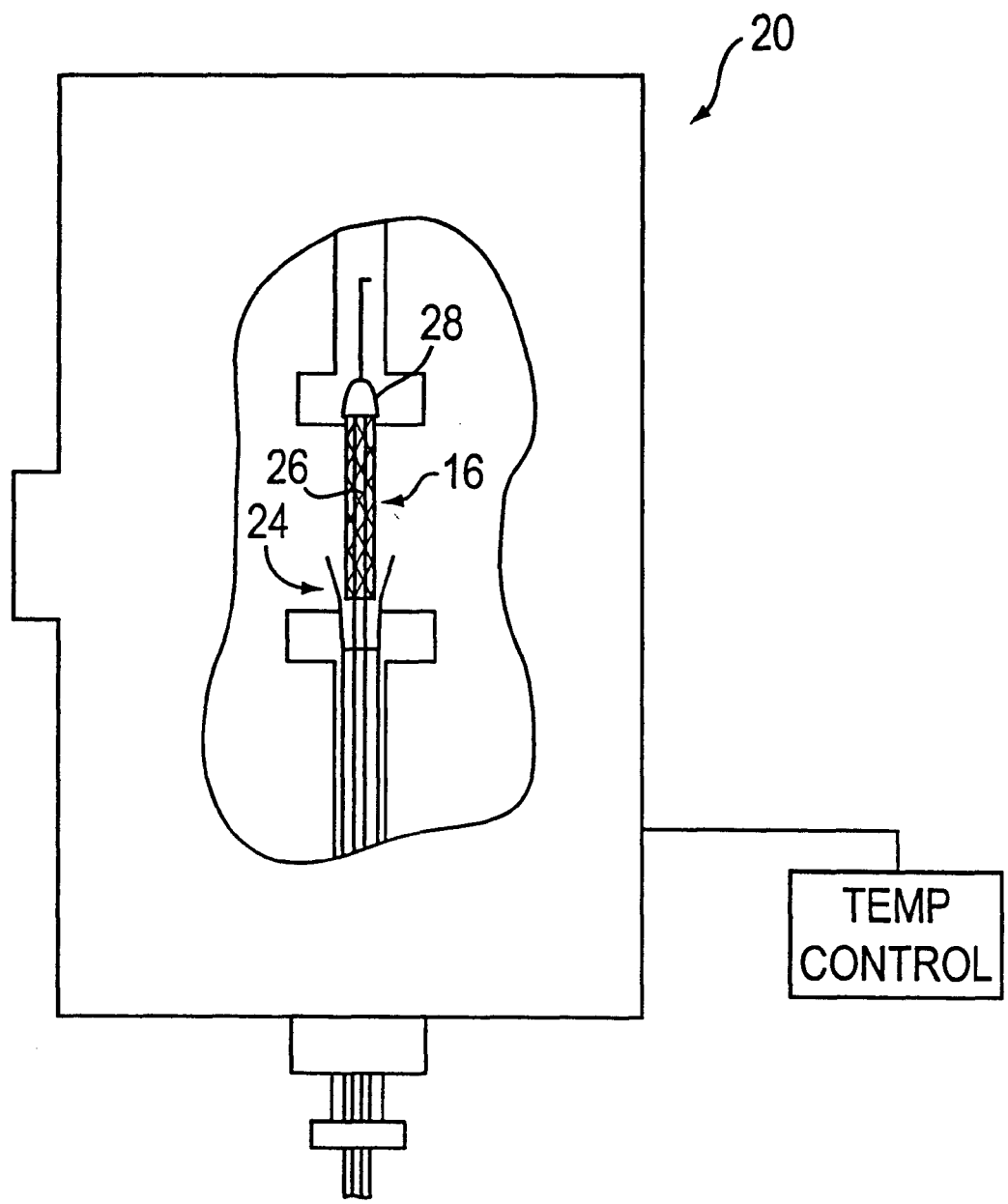
FIG. 4 is a schematic view showing a stent being re-sheathed after irradiation.

With reference to FIGS. 2–4, an exemplary stent deployment, irradiation, and recapture process will be described in greater detail. In this embodiment, the stent 16 is a mesh-like, shape memory metal stent. Nitinol is advantageous in that it is plastically deformable so that a stent formed therefrom can be substantially longitudinally compressed or collapsed and, upon removal of the compression force, will return to substantially its original configuration. This permits the stent to be collapsed during irradiation, so that irradiation time can be minimized. Nitinol is also characterized in that it will expand from a reduced diameter configuration, exhibited when it is maintained at a reduced temperature, to an enlarged diameter configuration when it is exposed to an elevated, e.g. body core, temperature. This characteristic makes nitinol an advantageous material for e.g. a vascular stent, since stents must be expanded in vivo from a reduced diameter to an enlarged diameter. The temperature dependent expansion of nitinol realizes that object. In accordance with the invention, the temperature related expansion of nitinol is exploited to facilitate deployment and re-capture/re-sheathing of the stent, as described in greater detail below. Indeed, in accordance with the invention, the cartridge holder defines a chamber which can be temperature controlled at least in the range of about 0° C. to 60° C., to selectively effect expansion and contraction of the stent structure. The holder also provides compressive force during the irradiation to prevent expansion of the stent due to instantaneous heating from the irradiation.

Figure 2A:
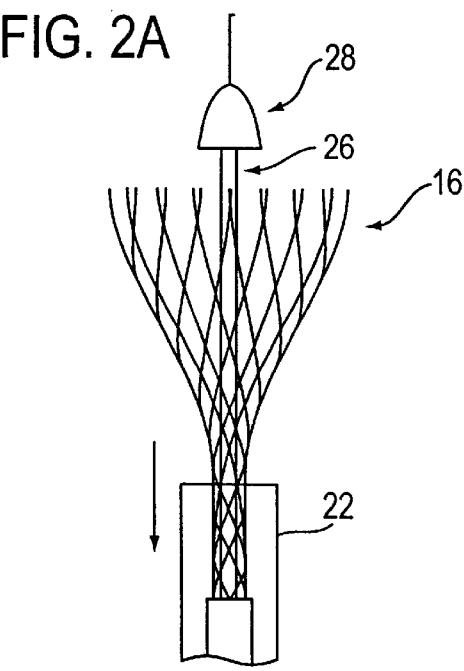

As shown in FIGS. 2 and 2A, the nitinol stent 16 is deployed at e.g. 40° C. using a commercially available mandril/sheath delivery system. Thus, as the sheath 22 is withdrawn, the stent 10, exposed to the elevated temperature prevailing in the cartridge 20, expands from its reduced, sheathed diameter to an enlarged diameter. Upon complete withdrawal of the sheath 22, the stent 16 will be disposed between the opposed plungers 10, 12 (FIG. 3).

Next the plungers 10, 12 are advanced towards one another to collapse the stent 16 therebetween, as shown in FIG. 3. To ensure that the stent will be fully collapsed, advantageously one of the plungers 12 has a larger diameter than the other so that the peripheral edges can overlap, as necessary or desirable. The collapsed stent is thus disposed in the path of the radiation beam 18 and irradiation of the stent 16 is initiated. The radiation beam is, for example, one of a gamma, electron, proton, deuteron and neutron beam. During irradiation, the stent 16 and/or cartridge 20 containing the same can be rotated and/or longitudinally translated to ensure irradiation of the entire stent structure.

Upon completion of the irradiation process, the stent must be redisposed in its sheath 22 for delivery to the patient. To that end, the plungers 10, 12 are shifted apart and the temperature of the cartridge interior is reduced to e.g. about 0° C. so as to facilitate return of the stent to its reduced diameter configuration, as shown in FIG. 4. The sheath 22 is then repositioned adjacent the longitudinal end of the stent 16 for receiving the same. To facilitate re-placement of the stent, a funnel tipped tube 24 may be disposed in surrounding relation to the sheath 22, as shown. Also, a clamping or other receiving structure (not shown in detail) within the sheath may engage and pull the stent thereinto. Even further, the mandrel 26 having an enlarged head 28 thereon, and/or the plunger 10, may be used to displace the stent 16 into the sheath 22.

Upon complete recapture, the sheath, mandrel and stent may then be suitably transported to the patient for stent placement.

As an alternative to the embodiments described above, two-way superelastic shape memory metals may be fabricated to contract at the higher temperature and expand at the lower temperature. Thus, in accordance with an alternate embodiment, the stent is collapsed at a high temperature (>60° C.) and expanded at a low temperature (37° C.). FIGS. 7A–7E illustrate this embodiment.

Figure 7A:
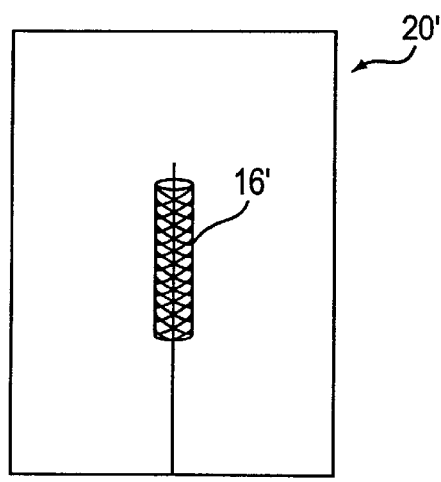
FIG. 7A is a schematic view showing a stent disposed in a cartridge holder in advance of irradiation, at room temperature.
Figure 7B:
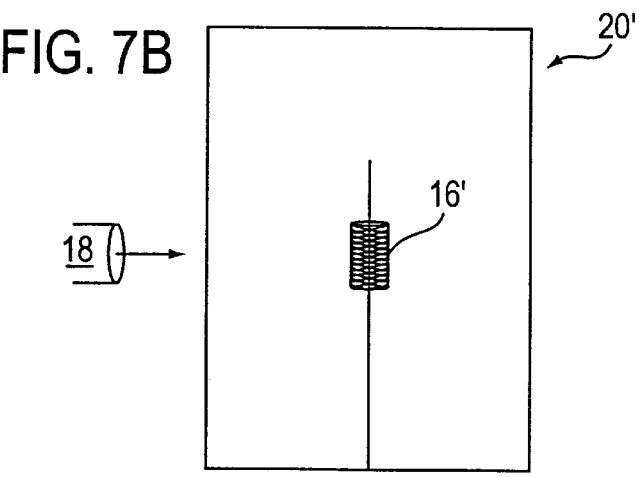
FIG. 7B is a schematic view showing the stent of FIG. 7A compressed in the radiation beam, due to heat generated by exposure to a suitable radiation beam.
Figure 7C:
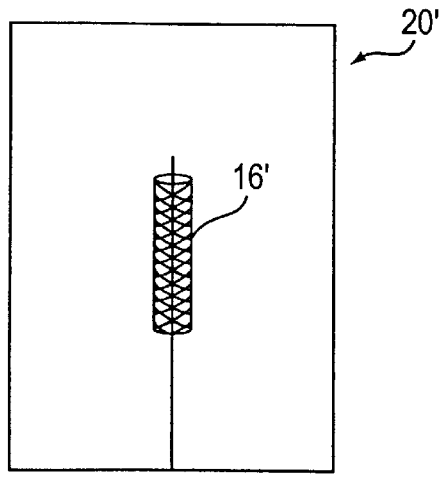
FIG. 7C is a schematic view showing the stent, re-expanded on cooling, following irradiation.
Figure 7D:
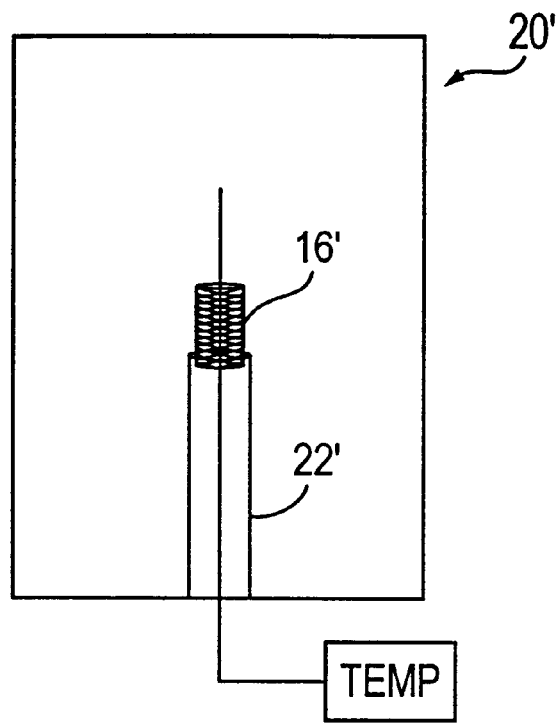
FIG. 7D is a schematic view showing the stent reduced in size on exposure to heat for re-sheathing.
Figure 7E:
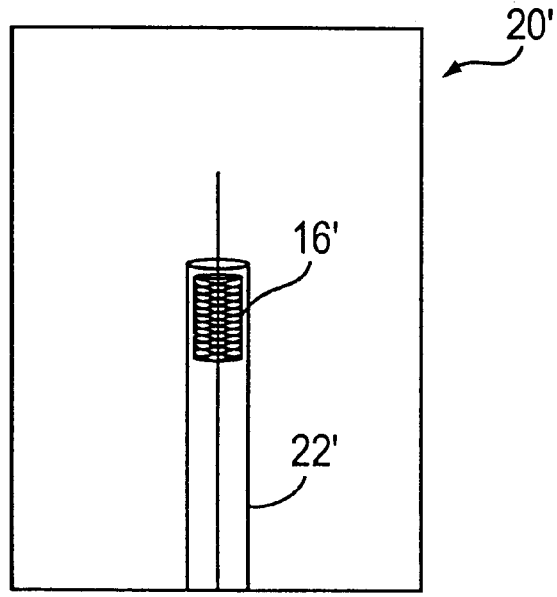
FIG. 7E is a schematic view showing the stent fully re-sheathed.

FIG. 7A shows the stent 16' expanded in its cartridge 20' at room temperature. FIG. 7B shows the stent compressed in the radiation beam 18. The radiation beam itself heats the stent. The collapse of the stent due to exceeding the shape transition temperature of the stent thereby gives the desired geometric compression which results in increased absorption of photons (in one example) by the stent 16'. After the radiation is completed, the stent cools and reexpands as shown in FIG. 7C. Now when it is desired to use the radioactive stent, the stent is heated, using either an electric current through the stent or applying a thermal heat source to the cartridge assembly. The stent 16' compresses and a sheath 22' may then be introduced, as shown in FIG. 7D, which will hold the stent compressed, as shown in FIG. 7E. The device is then ready for patient deployment.

Figure 5:
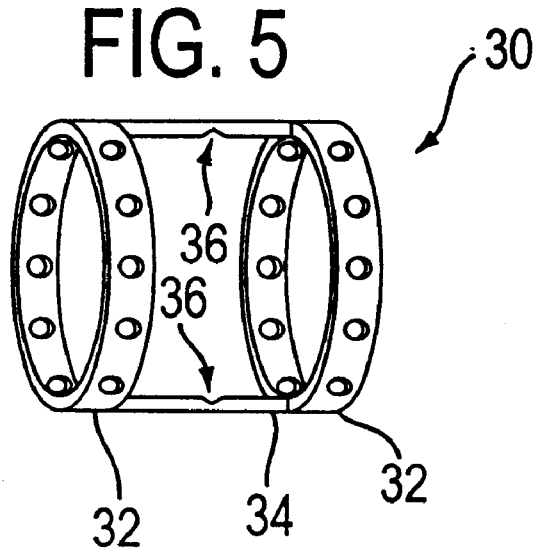
FIG. 5 is a schematic view, partly in section, of an accordion-type collapsible stent provided in accordance with the invention, in its longitudinally extended form.
Figure 6:
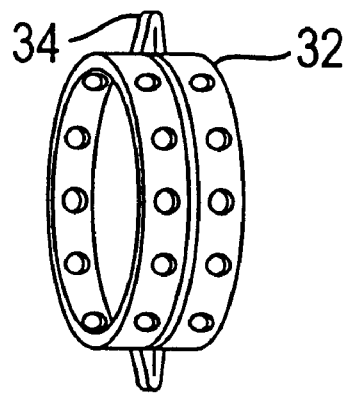
FIG. 6 is a schematic view, partly in section, of the stent of FIG. 5 in its longitudinally collapsed form.

In accordance with a further alternate embodiment, the stent 30 is defined by at least first and second circumferential ring structures 32 disposed at each longitudinal end of the stent assembly, with stays 34 extending therebetween to define the body of the stent, as shown in FIG. 5. The longitudinally extending stays 34 are selectively foldable or collapsible so that the circumferential rings 32 can be selectively disposed closer to each other thereby reducing the overall length of the stent, as shown in FIG. 6. In the illustrated embodiment, flex points are defined at least at the midpoint of the stay to 36 facilitate predictable collapse of the stays 34, either radially outwardly as shown or radially inwardly of the stent rings 32.

In the currently preferred, illustrated embodiments the stent structure is either porous or has pores defined therethrough to facilitate side branch and/or vessel sidewall perfusion and encapsulation as appropriate. To that end, the circumferential rings 32 and stays 34 may be formed of a mesh material. The use of a mesh material facilitates the selective accordion folding of the stays and subsequent expansion of the stent structure, and also enables blood flow through the stent wall. The material forming the stent may in this case be any metal or alloy with or without shape memory characteristics. This includes tantalum, gold, stainless steel, nitinol and rhenium.

While the invention has been described in connection with what is presently considered to be the most practical and preferred embodiments, it is to be understood that the invention is not to be limited to the disclosed embodiments, but on the contrary, is intended to cover various modifications and equivalent arrangements as will be appreciated by those of skill in the art to which it pertains.

We claim:

1. An apparatus for irradiating a stent structure to produce a radioactive stent structure comprising:

first and second plunger components, a plunger component support assembly for supporting said plunger components in opposed facing relation, at least one of said plunger components being movably mounted to said support assembly so as to be longitudinally displaceable towards the other of said plunger components to selectively capture a longitudinally collapsible stent structure therebetween; and means for producing a radiation beam directed at least at an area disposed between said plunger components so as to irradiate a stent structure disposed between said plunger components.

2. The apparatus of claim 1, wherein said support assembly comprises a housing defining an interior hollow chamber for receiving a stent structure to be irradiated, said at least one plunger component being movably mounted to a respective longitudinal end of said housing.

3. The apparatus of claim 2, further comprising a central mandril extending along the longitudinal axis of said housing, said plungers being mounted in telescoping, surrounding relation to said central mandril.

4. The apparatus of claim 2, further comprising means for controlling a temperature of said chamber of said housing.

5. The apparatus of claim 1, further comprising a stent delivery system including a shaft on which the stent structure is received and a sheath disposed coaxially to said shaft and sized to receive the stent therewithin.

6. The apparatus of claim 5, further comprising a receiver having a flared distal end and sized so as to be selectively disposed in surrounding relation to said sheath.

7. The apparatus of claim 5, wherein said shaft has an enlarged distal end for selectively engaging said stent structure to displace the same proximally into the sheath.

8. The apparatus of claim 1, wherein a distal end of one of said plungers has a transverse diameter larger than a transverse diameter of a distal end of the other of said plungers.

9. The apparatus of claim 1, in combination with a longitudinally collapsible stent structure disposed between said plunger components.

10. The apparatus of claim 9, wherein said stent structure is formed at least in part from a shape memory metal.

11. The apparatus of claim 9, wherein said stent structure is formed at least in part from a material selected from the group consisting of tantalum, gold, stainless steel, nitinol and rhenium.

12. The apparatus of claim 9, wherein the stent structure is constructed and arranged to telescopingly collapse from at least one end thereof.

13. The apparatus of claim 9, wherein the stent structure comprises first and second circumferential ring structures disposed at each longitudinal end thereof and at least two stay elements extending therebetween to define a main body thereof, each said stay element being selectively foldable whereby said circumferential rings are selectively disposed adjacent each other thereby reducing an overall length of the stent structure.

14. The apparatus of claim 9, wherein said stent structure is porous and/or has apertures defined therethrough.

15. The apparatus of claim 9, wherein said stent structure is formed from a mesh material.

16. The apparatus of claim 9, wherein said stent structure is formed from nitinol whereby said stent can be substantially longitudinally collapsed and upon removal of a compression force returned to substantially an original configuration thereof.

17. A method for irradiating a stent structure to produce a radioactive stent structure comprising:

providing an apparatus comprising first and second plunger components; a plunger component support assembly for supporting said plunger components in opposed facing relation; at least one of said plunger components being movably mounted to said support assembly so as to be longitudinally displaceable towards the other of said plunger components to selectively capture a longitudinally collapsible stent structure therebetween;

disposing a stent structure between said plunger components;

displacing at least one of said plunger components toward the other so that said stent structure is engaged and held therebetween;

producing a radiation beam and directing said beam toward said stent structure disposed between said plunger components; and rotating said plunger components about a longitudinal axis thereof and/or moving said plunger components longitudinally so as to irradiate at least a portion of said stent structure.

18. The method of claim 17, further comprising longitudinally collapsing said stent structure between said plunger components during said displacing step.

19. The method of claim 17, wherein said providing step comprises providing a support assembly that includes a housing defining an interior hollow chamber for receiving the stent structure to be irradiated, said at least one plunger component being movably mounted to a respective longitudinal end of said housing.

20. The method of claim 19, further comprising controlling a temperature of an interior of said chamber of said housing.

21. The method of claim 17, further comprising providing a stent delivery system including a shaft on which the stent structure is received and a sheath disposed coaxially to said shaft and sized to receive the stent therewithin, and wherein said disposing step comprises advancing said stent delivery system through a passage defined in one of said plunger components, retracting said sheath, and radially expanding said stent structure.

22. The method of claim 19, wherein said housing is translated longitudinally and/or rotated relative to the radiation beam with said plunger components.

* * * * *